US012605204B2

(12) United States Patent
Bukesov et al.

(10) Patent No.: US 12,605,204 B2
(45) Date of Patent: Apr. 21, 2026

(54) LASER-INDUCED FLASHING ALERT, CONTROL, OR COMPENSATION

(71) Applicant: GYRUS ACMI, INC., Westborough, MA (US)

(72) Inventors: Sergey A. Bukesov, Acton, MA (US); Kurt G. Shelton, Bedford, MA (US); Maria Rao, Worcester, MA (US); David Bloem, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 430 days.

(21) Appl. No.: 17/815,989

(22) Filed: Jul. 29, 2022

(65) Prior Publication Data

US 2023/0033644 A1     Feb. 2, 2023

Related U.S. Application Data

(60) Provisional application No. 63/203,848, filed on Aug. 2, 2021.

(51) Int. Cl.
| | |
|---|---|
| *A61B 18/20* | (2006.01) |
| *A61B 1/00* | (2006.01) |
| *A61B 1/045* | (2006.01) |
| *A61B 1/06* | (2006.01) |

(52) U.S. Cl.
CPC ........ *A61B 18/201* (2013.01); *A61B 1/00045* (2013.01); *A61B 1/045* (2013.01); *A61B 1/0646* (2013.01); *A61B 1/0655* (2022.02)

(58) Field of Classification Search
None
See application file for complete search history.

(56) References Cited

U.S. PATENT DOCUMENTS

| | | | |
|---|---|---|---|
| 10,595,708 B2 | 3/2020 | Kojima | |
| 2011/0074943 A1* | 3/2011 | Modell | ................ H04N 25/531 |
| | | | 348/E7.085 |
| 2018/0344405 A1 | 12/2018 | Brown et al. | |
| 2020/0234439 A1 | 7/2020 | Chang et al. | |
| 2020/0397249 A1* | 12/2020 | Talbert | .................. A61B 1/045 |
| 2021/0038064 A1 | 2/2021 | Shelton et al. | |

(Continued)

FOREIGN PATENT DOCUMENTS

| | | |
|---|---|---|
| DE | 102022119170 | 2/2023 |
| JP | 2010042182 | 2/2010 |
| JP | 2011104199 | 6/2011 |

(Continued)

OTHER PUBLICATIONS

"Indian Application Serial No. 202244043911, First Examination Report mailed Aug. 2, 2023", 5 pgs.

(Continued)

*Primary Examiner* — Michael T. Holtzclaw
(74) *Attorney, Agent, or Firm* — Schwegman Lundberg & Woessner, P.A.

(57) ABSTRACT

A system for endoscopically imaging a first target of a patient, using a light source and a light detector, and for laser-treating a same or different second target of the patient, using a laser source, the system. For example, the system can have at least signal processing circuitry, which can include a target response signal laser-source flashing component detector and a flashing analyzer.

19 Claims, 12 Drawing Sheets

(56) References Cited

U.S. PATENT DOCUMENTS

| | | | | |
|---|---|---|---|---|
| 2022/0354578 A1* | 11/2022 | Cook | .................... | A61B 18/26 |
| 2024/0016543 A1* | 1/2024 | Altshuler | .............. | A61B 18/22 |

FOREIGN PATENT DOCUMENTS

| | | | |
|---|---|---|---|
| JP | 2012050601 | | 3/2012 |
| JP | 2013506498 | A | 2/2013 |
| JP | 2016209001 | | 12/2016 |
| JP | 2017527137 | A | 9/2017 |
| JP | 2023021951 | | 2/2023 |
| JP | 7459183 | B2 | 3/2024 |
| JP | 2024071453 | A | 5/2024 |
| JP | 7646907 | B2 | 3/2025 |
| JP | 2025083377 | A | 5/2025 |
| JP | 2026012347 | | 1/2026 |

OTHER PUBLICATIONS

"Japanese Application Serial No. 2022-122904, Notification of Reasons for Rejection mailed Sep. 5, 2023", w English Translation, 7 pgs.

"Japanese Application Serial No. 2024-043860, Notification of Reasons for Refusal mailed Sep. 10, 2024", w/ English Translation, 6 pgs.

"Japanese Application Serial No. 2024-043860, Voluntary Amendment Filed Apr. 25, 2024", w/ english claims, 12 pgs.

"Canadian Application Serial No. 3,169,384, Office Action mailed Sep. 26, 2023", 4 pgs.

"Japanese Application Serial No. 2022-122904, Response filed Nov. 29, 2023 to Notification of Reasons for Rejection mailed Sep. 5, 2023", w english claims, 11 pgs.

"Canadian Application Serial No. 3,169,384, Response filed Jan. 17, 2024 to Office Action mailed Sep. 26, 2023", 13 pgs.

"Indian Application Serial No. 202244043911, Response filed Jan. 9, 2024 to First Examination Report mailed Aug. 2, 2023", 22 pgs.

"Indian Application Serial No. 202244043911, Hearing Notice mailed Feb. 25, 2025", 2 pgs.

"Japanese Application Serial No. 2024-043860, Response filed Dec. 2, 2024 to Notification of Reasons for Refusal mailed Sep. 10, 2024", w/ english claims, 9 pgs.

"Indian Application Serial No. 202244043911, Response filed Mar. 27, 2025 to Hearing Notice mailed Feb. 25, 2025", w/ claims, 30 pgs.

"Japanese Application Serial No. 2025-183519, Voluntary Amendment Filed Nov. 11, 2025", w claims, 12 pgs.

* cited by examiner

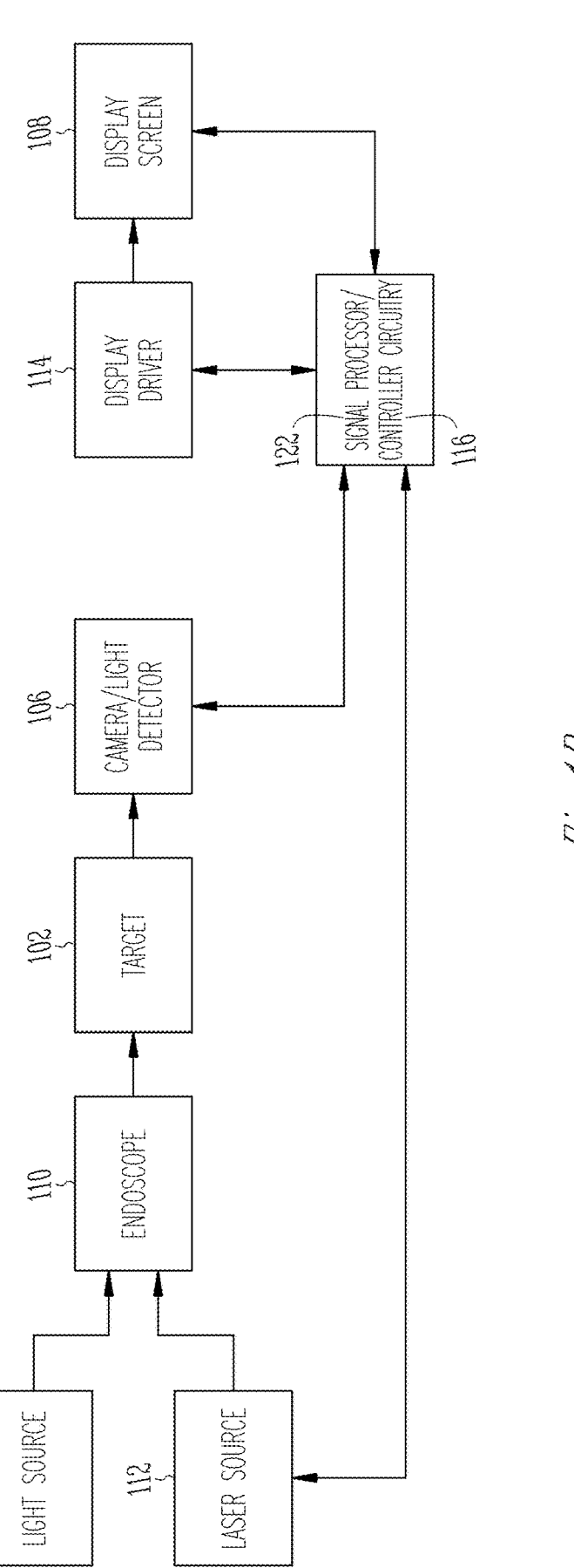
*Fig. 1B*

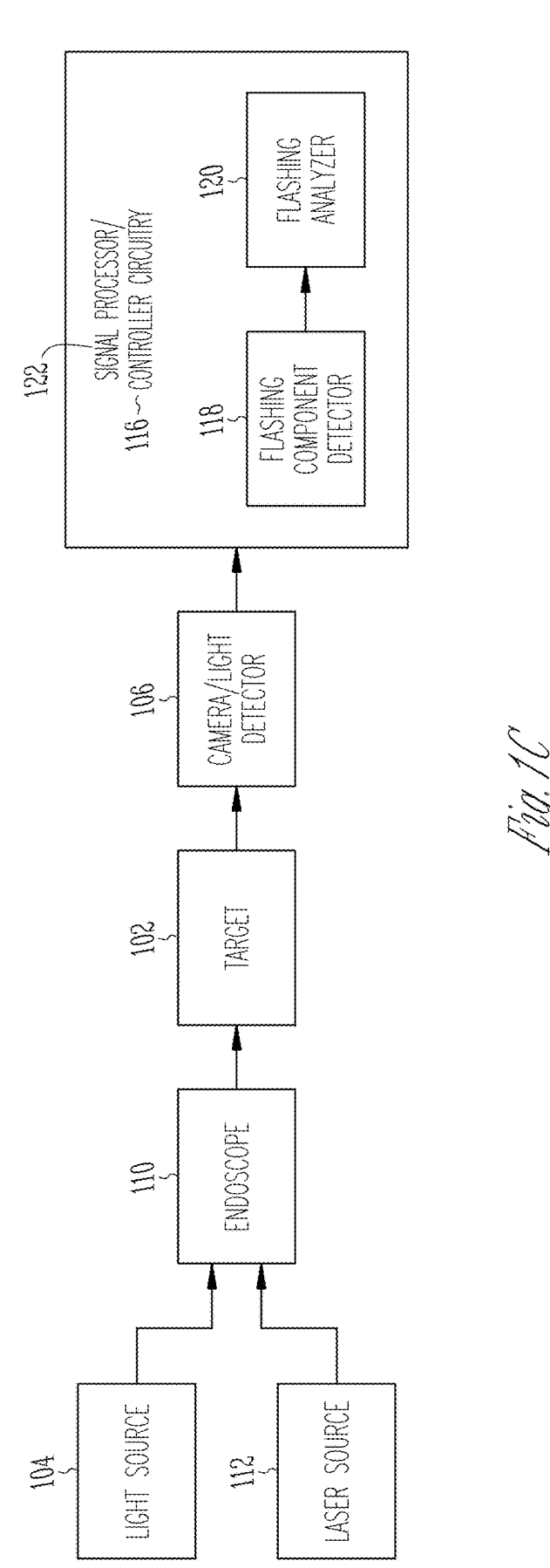
*Fig. 1C*

FLASHING COMPONENT DETECTOR~118
OR FLASHING ANALYZER~120
OF SIGNAL PROCESSOR/CONTROLLER CIRCUITRY~116

CAMERA OR
LIGHT DETECTOR

106

SPECTROMETER

402

RESPONSE
LIGHT
WAVELENGTH FILTER

302

INTEGRATOR/
ACCUMULATOR

304

DISPLAY
DRIVER

114

DISPLAY
SCREEN

108

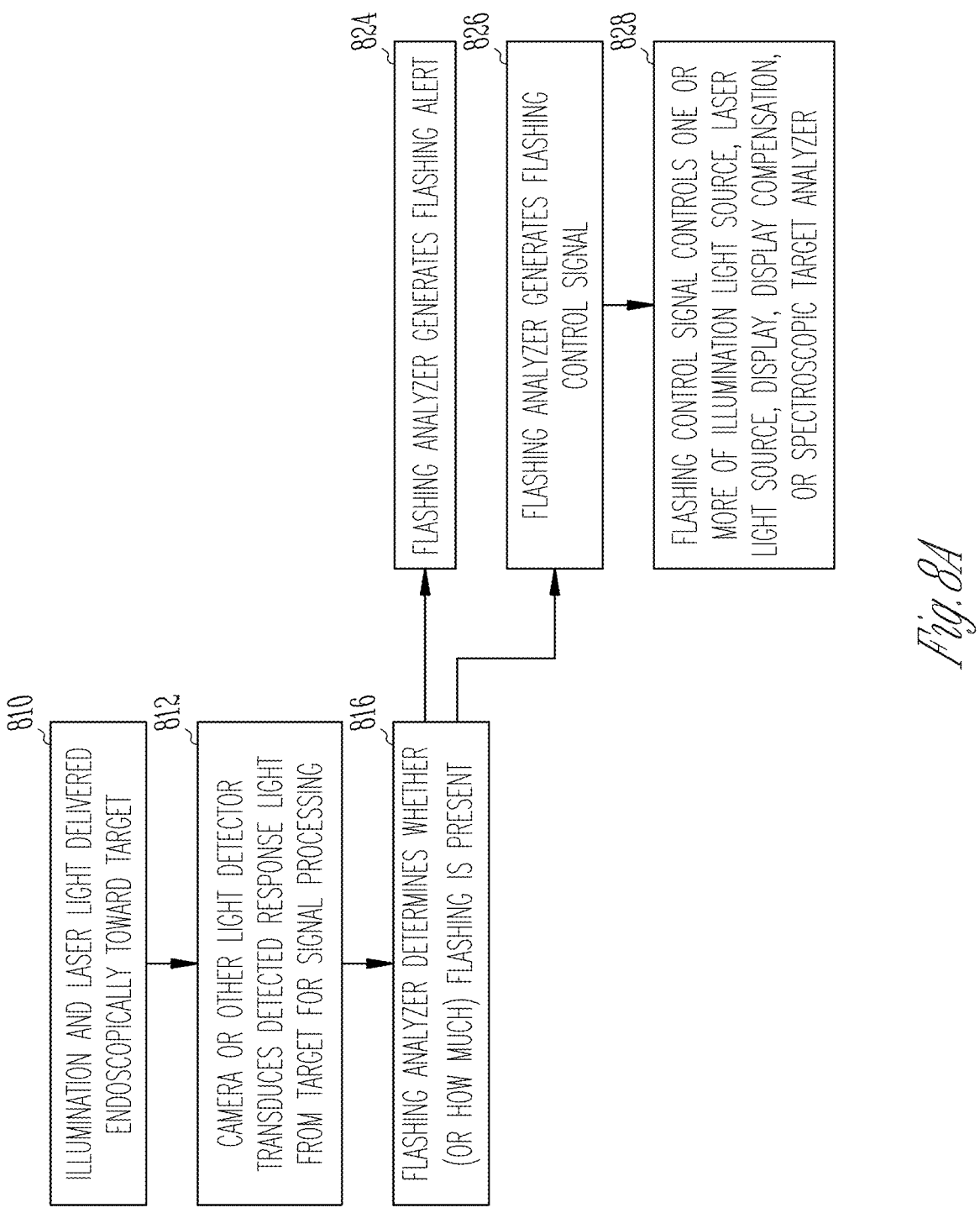

810 ILLUMINATION AND LASER LIGHT DELIVERED ENDOSCOPICALLY TOWARD TARGET

812 CAMERA OR OTHER LIGHT DETECTOR TRANSDUCES DETECTED RESPONSE LIGHT FROM TARGET FOR SIGNAL PROCESSING

816 FLASHING ANALYZER DETERMINES WHETHER (OR HOW MUCH) FLASHING IS PRESENT

824 FLASHING ANALYZER GENERATES FLASHING ALERT

826 FLASHING ANALYZER GENERATES FLASHING CONTROL SIGNAL

828 FLASHING CONTROL SIGNAL CONTROLS ONE OR MORE OF ILLUMINATION LIGHT SOURCE, LASER LIGHT SOURCE, DISPLAY, DISPLAY COMPENSATION, OR SPECTROSCOPIC TARGET ANALYZER

Fig. 8A

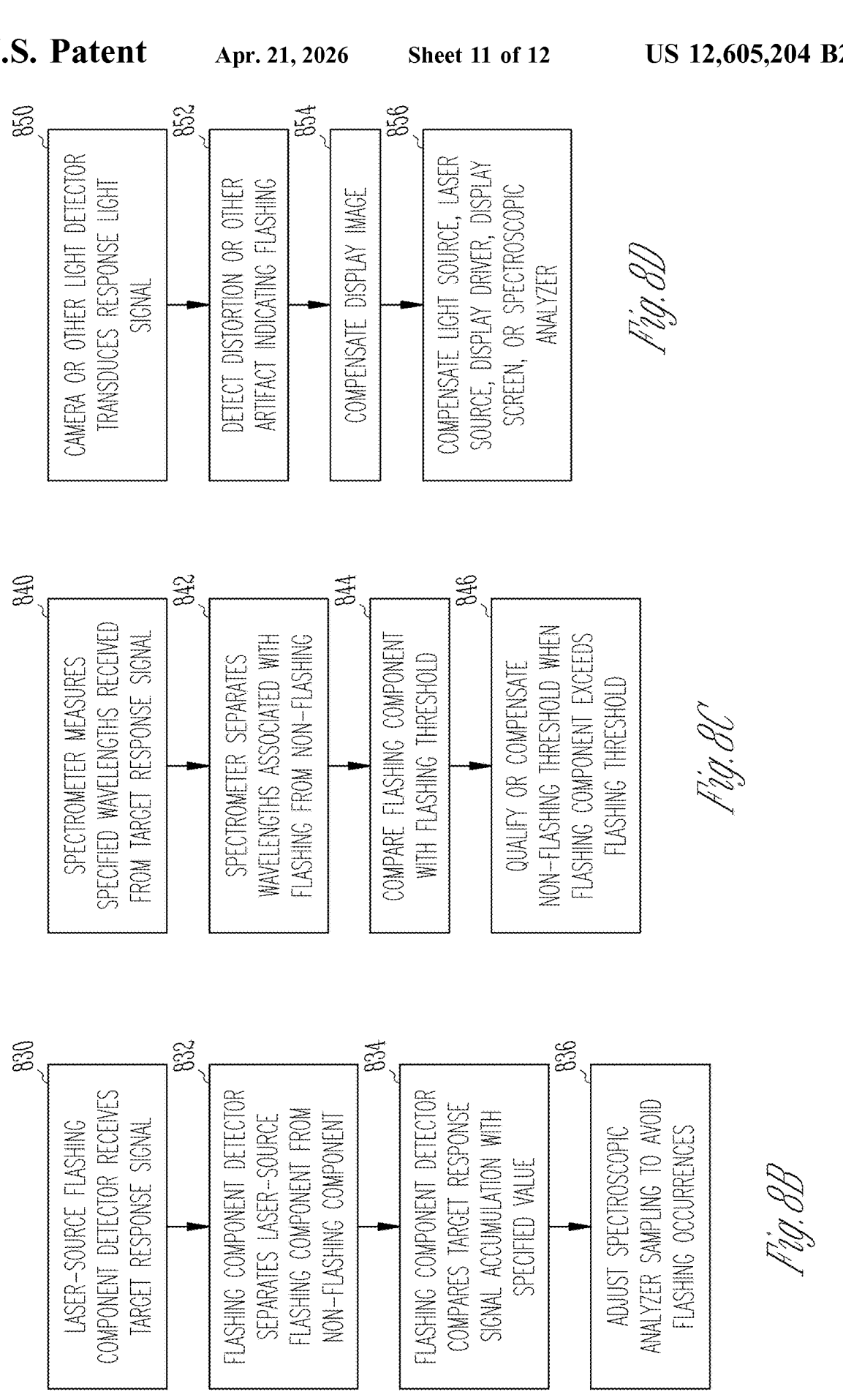

850 CAMERA OR OTHER LIGHT DETECTOR TRANSDUCES RESPONSE LIGHT SIGNAL

852 DETECT DISTORTION OR OTHER ARTIFACT INDICATING FLASHING

854 COMPENSATE DISPLAY IMAGE

856 COMPENSATE LIGHT SOURCE, LASER SOURCE, DISPLAY DRIVER, DISPLAY SCREEN, OR SPECTROSCOPIC ANALYZER

Fig.8D

840 SPECTROMETER MEASURES SPECIFIED WAVELENGTHS RECEIVED FROM TARGET RESPONSE SIGNAL

842 SPECTROMETER SEPARATES WAVELENGTHS ASSOCIATED WITH FLASHING FROM NON-FLASHING

844 COMPARE FLASHING COMPONENT WITH FLASHING THRESHOLD

846 QUALIFY OR COMPENSATE NON-FLASHING THRESHOLD WHEN FLASHING COMPONENT EXCEEDS FLASHING THRESHOLD

Fig.8C

830 LASER-SOURCE FLASHING COMPONENT DETECTOR RECEIVES TARGET RESPONSE SIGNAL

832 FLASHING COMPONENT DETECTOR SEPARATES LASER-SOURCE FLASHING COMPONENT FROM NON-FLASHING COMPONENT

834 FLASHING COMPONENT DETECTOR COMPARES TARGET RESPONSE SIGNAL ACCUMULATION WITH SPECIFIED VALUE

836 ADJUST SPECTROSCOPIC ANALYZER SAMPLING TO AVOID FLASHING OCCURRENCES

ACCUMULATOR ACCUMULATES
WAVELENGTHS ASSOCIATED WITH
FLASHING COMPONENT OF TARGET
RESPONSE SIGNAL

920

ACCUMULATED FLASHING COMPONENTS
COMPARED WITH THRESHOLD

930

FLASHING ALERT OR CONTROL SIGNAL
IS GENERATED IN RESPONSE TO
FLASHING INDICATED BY COMPARISON

LASER-INDUCED FLASHING ALERT, CONTROL, OR COMPENSATION

TECHNICAL FIELD

This document pertains generally, but not by way of limitation, to systems and methods to help reduce the displayed visual effects of undesired laser-induced emissions, such as during an endoscopic or a similar minimally-invasive or other surgical treatment of at least one of hard or soft tissue in a human or other animal.

BACKGROUND

Spectroscopy and spectrometry can be used to help identify one or more materials through the visible light or other electromagnetic spectrum reflected or otherwise scattered, transmitted, or absorbed by a material. Spectroscopy can be used to help identify and treat one or more anatomical structures within an animal such as a human being.

In certain endoscopic techniques, light from a visualization illumination light source and a laser source can be introduced endoscopically into a cavity of an animal. The light from the illumination light source can be used to illuminate the cavity and the light from the laser source can be used for treating a targeted anatomical structure or other region of interest. During treatment of the targeted anatomical structure, a laser-induced emission ("flashing") may be observed on a display screen being used to display an image of response light arriving at a photodetector or at a photo-imaging device from the targeted region of interest. Such response light can be signal-processed and displayed or analyzed, or both, such as can include using one or more spectroscopic techniques. Flashing can result from, for example, combustion reaction of material decomposition, liquid luminescence cavitation, laser induced breakdown emission, or burning off of dirt or other contaminant such as can be located on a working tip of a laser fiber used for optically coupling light from the laser-source to the target region.

When flashing occurs, it can interfere with an imaging signal being displayed, a spectroscopic signal being analyzed, or both. For example, flashing can produce a distortion artifact that can be visible on the image of the target region being displayed visually on a display screen, or flashing can produce an inconsistent spectroscopic reading of a photodetector receiving light from the target region of interest. Such distortion artifacts or other anomalous responses due to laser-source flashing can be undesirable during a diagnostic or treatment procedure.

DESCRIPTION OF THE FIGURES

FIG. 1b illustrates a system for endoscopically imaging a target with signal processor/controller circuitry to control various outputs.

FIG. 1c illustrates a system for endoscopically imaging a target with signal processor/controller circuitry to detect flashing.

FIGS. 8a, 8b, 8c and 8d depict methods of detecting and controlling laser-sourced flashing.

DETAILED DESCRIPTION

This document describes, among other things, an endoscopic or other system for imaging and laser-treating one or more target regions of interest. The system can include a light source and a light detector, such as for respective illumination and visualization of a target region of interest. The system can also include a laser source, such as for delivering laser energy to the target region of interest. The system can include a laser-source flashing component detector, such as for generating a flashing alert or flashing control signal based on how much flashing is occurring. The flashing alert or flashing control signal, in turn, can be used to improve a displayed image of one or more target regions, to alert a user, or to control or compensate componentry of the system. How much flashing is occurring can be determined using one or more techniques, such as explained herein. For example, a spectroscopic filter or analyzer can accumulate response light wavelengths occurring outside of a spectral band of the illuminating light source, with such accumulated response light wavelengths providing an indication of how much laser-source-induced flashing is occurring. Alternatively or additionally, an amount of displayed distortion artifact (e.g., saturated rows of pixels) on an imaging channel or display screen can be used as an indication of how much laser-source-induced flashing is occurring. Other examples and details are explained further below.

Figure 1A:
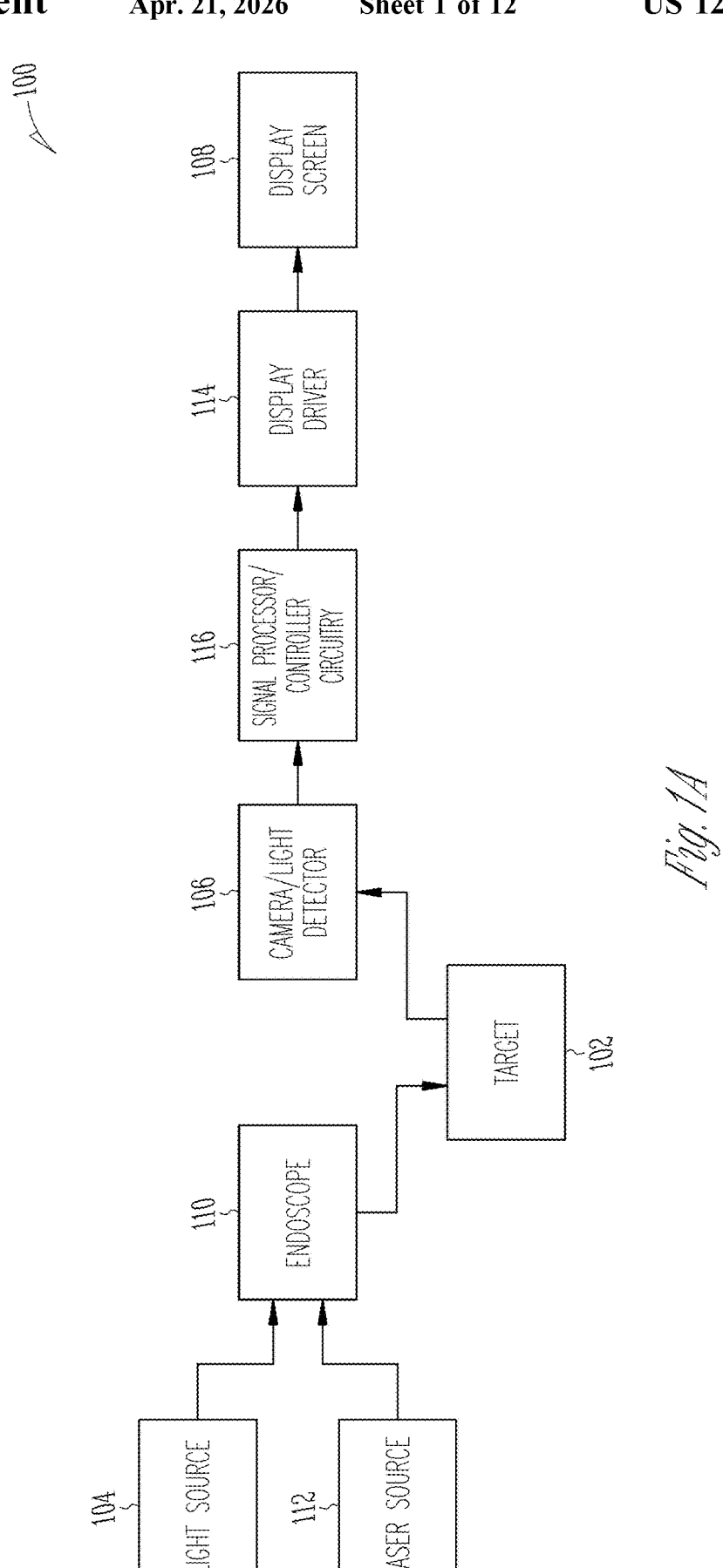
FIG. 1a illustrates a system for endoscopically imaging a target.

FIG. 1a shows an example of portions of a system 100, such as can be used for imaging and laser-treating one or more regions of interest, such as a target 102 in a human or other animal patient or subject, or other target 102. Portions of the system 100 can be included in or coupled to a delivery device, such as an endoscope 110, such as for treating a target 102 located internally within a subject. This can be assisted by accompanying visualization or imaging, which, in turn, can be assisted by illumination of such an internal target 102 or region of interest such as a nearby cavity or other surroundings.

In FIG. 1a, the system 100 can include an illumination light source 104, such as can provide broadband illumination (e.g., including light at human-visible wavelengths, such as from about 380 nm to 740 nm) to the internal target 102. Such illumination can help allow visualization or imaging of the target 102, such as using a light detector or imaging pixel array ("camera") 106. The light detected at the camera 106, such as for visualization or imaging, can be detected and transduced and provided as an electronic response signal. For example, this electronic response signal can represent one or a video sequence of a plurality of two-dimensional (2D) image frames, which can be provided to a display driver 114 such as for display on a display screen 108.

The illumination light from the illumination light source 104 can be provided to the internal target 102, such as via one or more optical fibers or other illumination optics of the endoscope 110 or other delivery system. A distal portion of the endoscope 110 can be inserted into the subject, such as via an orifice or incision. Laser light from a laser source 112 can also be provided via the endoscope 110 or other delivery system such as to treat the target 102. For example, such laser treatment can include laser lithotripsy such as to help break up a biological calculus (sometimes referred to as a "stone") at the target 102. Other laser treatment procedures can include treating tumors or precancerous growths or cauterizing a vessel or tissue within a patient.

In FIG. 1b, controller circuitry 116 can be included in the system 100, such as to help operate one or more components such as the laser source 112, the light source 104, or other components. The controller circuitry 116 can also help signal-process any response light signals detected and transduced by the camera 106 or other light detector. The controller circuitry 116 can include or be coupled to componentry for at least one of detecting, measuring, or analyzing whether laser-source flashing is occurring such as for generating a flashing alert or flashing control signal based on how much flashing is occurring, such as explained further below. The flashing alert or flashing control signal, in turn, can be used to improve a displayed image of one or more target regions, to alert a user, or to control or compensate componentry of the system, such as explained further below.

Flashing is a reflective emission from the target 102 that can be produced when the laser-source 112 delivers energy to treat the target 102. However, flashing can be an undesirable biproduct of laser treatment because, for example, it can interfere with user visualization or imaging display of the target 102 or its surroundings during the treatment procedure.

In FIG. 1c, the signal processing circuitry 122 can be coupled to receive an electrically-transduced indication of response light from the target 102 from the camera 106 or other light detector. This indication of response light can include a response light component due to laser-source flashing and a response light component that is not due to laser-source flashing. The signal processing circuitry 122 can include a flashing analyzer 120, which can include or can be coupled to a flashing component detector 118, such as to detect or differentiate the flashing component of the response light from the non-flashing component of the response light. For example, response light at wavelengths longer than a specified first threshold value (e.g., greater than a first threshold value of 720 nm) can be deemed to represent the flashing component of the response light, and response light at wavelengths shorter than the first threshold value (e.g., shorter than the first threshold value of 720 nm) can be deemed to represent the non-flashing component of the response light. For example, the non-flashing component of the response light may include response light received in response to the illumination light from the light source 104, or response light carrying spectroscopic information about one or more component analyte materials of the target 102.

Figure 2:
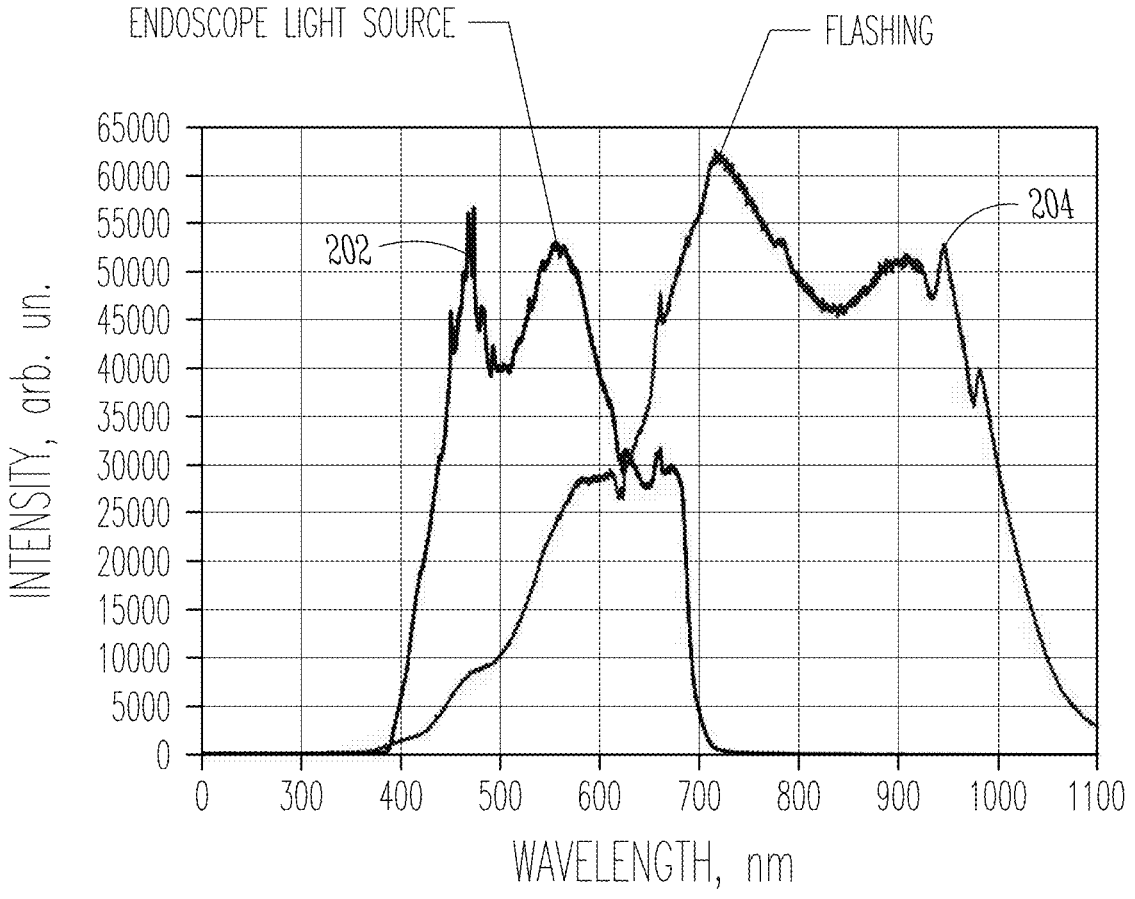
FIG. 2 illustrates a computer-modeled graph of response light intensity vs. response light wavelength.

FIG. 2 shows an example of a computer-modeled graph of response light intensity versus response light wavelength when a target 102 is illuminated by both an illumination light source 104 and a treatment laser-source 112 during a procedure. In FIG. 2, a non-flashing component 202 of the response light from the endoscope light source 104 predominates at wavelengths less than 625 nanometers, which can be specified as the first threshold referred to above. A flashing component 204 from the laser-source 112 predominates at wavelengths greater than 625. As explained above, the flashing component 204 can occur from a scattering of light during decomposition of, for example, biological material. The flashing component 204 can also occur from burning of the laser fiber. As indicated in FIG. 2, the flashing component 204 can be more intense than the intensity of the response light due to illumination by the endoscopic light source 202.

Using the system illustrated in at least one of FIGS. 1a, 1b and 1c, by accumulating or integrating response light spectral energy at such wavelengths that are longer than the first threshold value, a total flashing amount can be determined. This total flashing amount, in turn, can optionally be compared (e.g., such as using a comparator) to a specified second threshold value. The specified second threshold value can either be either an absolute second threshold value or a relative second threshold value. For example, a relative second threshold value can be specified relative to the non-flashing component of the response light or relative to a total amount of the response light including both flashing and non-flashing components. When the total flashing amount exceeds the second threshold value, a flashing alert or flashing control signal can be generated to signal this. The flashing alert can be displayed or otherwise used to inform a user, for example, that imaging or visualization is being affected by laser-source flashing. The flashing control signal can be used to adjust one or more other components, such as to compensate for an effect of such laser-source flashing, such as explained further below. The flashing control signal need not be generated as a result of comparison to the second threshold, for example, a non-thresholded indication of the total flashing can be used to generate the control signal, if desired, such as for compensating one or more other components for the effect of laser-source flashing.

Figure 3:
FIG. 3 illustrates an example of portions of the flashing component detector or flashing analyzer.

FIG. 3 illustrates an example of portions of the flashing component detector 118 or flashing analyzer 120 in more detail, which can receive a signal indicative of response light from a camera or light detector 106. The flashing component detector or flashing analyzer 120 can include a response light wavelength filter 302, such as to help separate the laser-source flashing component of the target response signal from the non-flashing component of the target response signal. An integrator or accumulator 304 can be coupled to the output of the filter 302, such as to accumulate spectral energies at a multiple wavelengths exceeding the wavelength of the first wavelength threshold.

The accumulator 304 can generate a response within the system 100 indicating the amount of flashing occurring. For example, the accumulator 304 can cumulate at least one of the portions of the flashing signal associated with the intensity of the wavelengths received from the camera or light detector 106. Optionally, the accumulator 304 can also cumulate durations of the response light including wavelengths associated with flashing. In an example, the accumulator 304 can cumulate saturated or similar pixel intensities (e.g., flashing may induce pixel saturation occurring in pixel rows), durations, or pixel counts associated with flashing, such as can be obtained from the display screen 108 or from a display driver driving the pixels of the display screen 108. Alternatively or additionally, the accumulator 304 can perform weighted or unweighted cumulation of at least one spectrometer 402 reading at one or more specified wavelengths or wavelength bands. A flashing alert or flashing control signal can be generated based on the output of the integrator or accumulator 304, and provided to the user, such as an alert, or to other componentry, such as a flashing control signal. For example, such a flashing control signal can be used for compensating the display driver driving the display screen 108 by substituting non-saturated pixels for flashing-saturated pixels. In an example, such a flashing control signal can be used for compensating the camera or light detector 106, such as explained further below.

Figure 4:
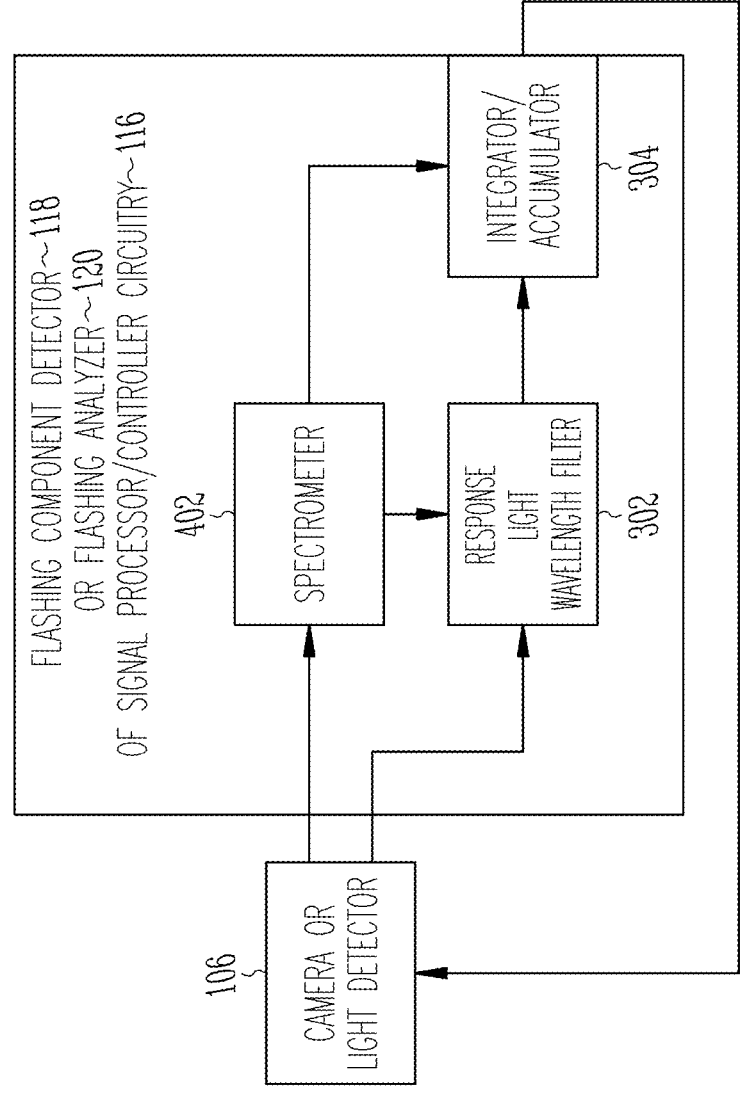
FIG. 4 illustrates an example of portions of the flashing component detector or flashing analyzer.

FIG. 4 illustrates an example of portions of the signal processor 122 or controller circuitry 116 in more detail, such as can include the one or both of the flashing component detector 118 and the flashing analyzer 120. A spectrometer 402 or other narrow band optical detector can be included, such as to help spectrometrically separate wavelengths associated with the laser-source flashing component of the target response signal from wavelengths associated with the non-flashing component of the target response signal. The spectrometer 402 can be coupled to an integrator/accumulator 304, either directly, via the response light wavelength filter 302, or both. The response light wavelength filter 302 can then be coupled with the accumulator 304. The accumulator 304 can provide an indication of flashing amount, which can be compared to a threshold value or otherwise signal-processed and used to control the light detector 106 such as to control the response from the light detector based on the flashing and non-flashing components received from the light detector 106.

Figure 5:
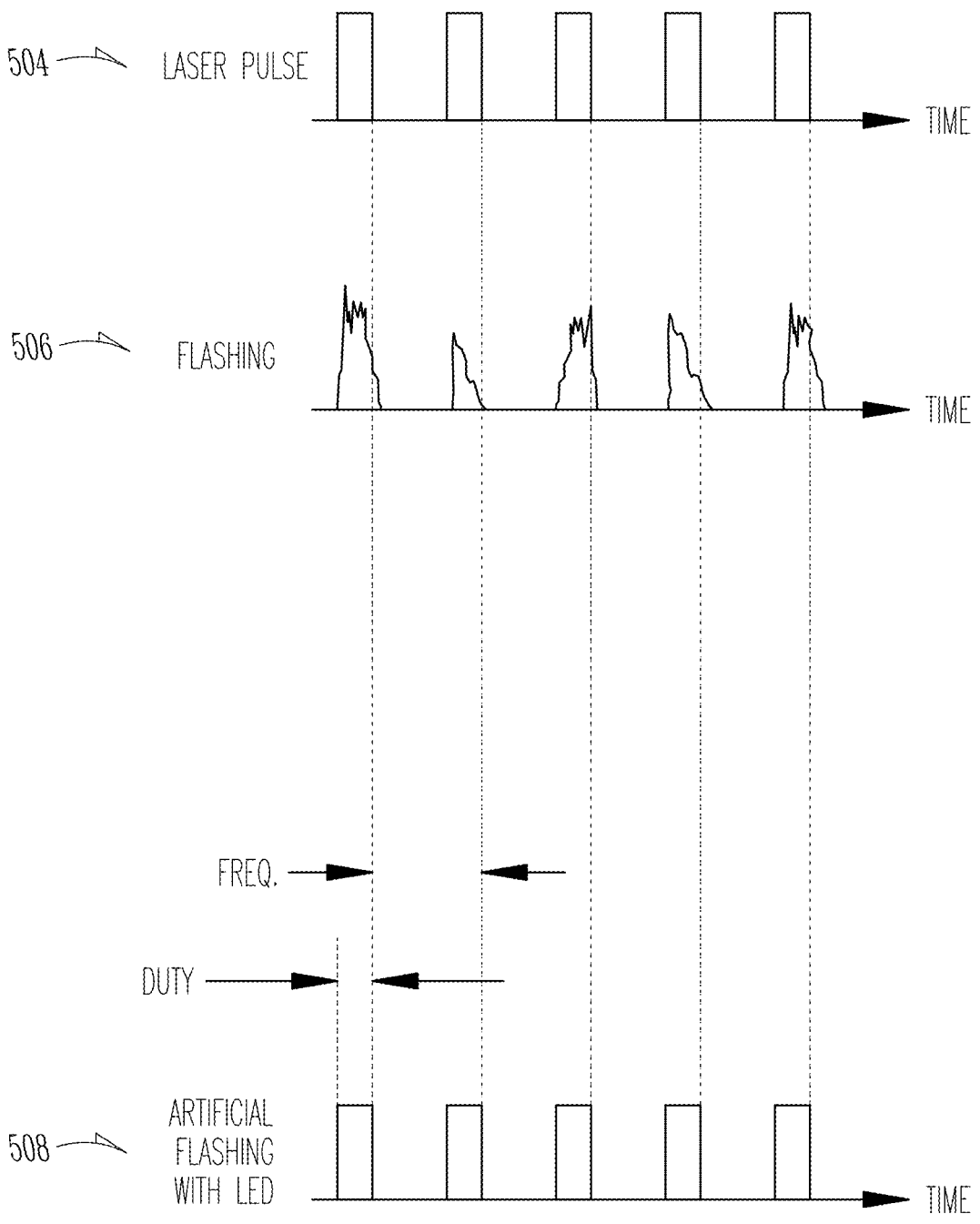
FIG. 5 illustrates an example of portions of the flashing component.

FIG. 5 illustrates a conceptualized timing diagram example of operating portions of the system 100. At 504, a series of laser pulses are shown as being issued by a lithotripsy laser, such as to help break up a calculus of "stone." At 506, a series of corresponding resulting laser flashing instances are shown, of varying intensities and durations. Various factors can come into play in affecting the amount (intensity and duration) of flashing, including contaminants or other materials present near the tip of the laser fiber, previous degradation of the laser fiber, or other factors, such as explained herein. At 508, a series of flashing detection indication pulses can be generated by the system 100. This can include using the camera 106 to detect light from the target region of interest, and bandpass filtering and accumulating detected light at wavelengths exceeding a "flashing threshold" wavelength. As explained, the "flashing threshold" wavelength can be selected to be capable of discriminating between detected light due to flashing and detected light due to an endoscopic illumination light source. At 508, the various flashing detection indication pulses can have a pulsewidth and repetition frequency that may follow those parameters of corresponding laser pulses 504 causing the flashing occurrences. But not all laser pulses 504 will necessarily result in flashing occurrences 506 and resulting flashing detection indication pulses 508. Moreover, the pulsewidth/duty of the resulting flashing detection indication pulses 508 may vary, such as depending on how much flashing is occurring. Flashing instances 506 occur when the intensity of light detected by the camera 106 exceeds a specified flashing threshold value. In FIG. 5, the duration of a particular flashing instance 508 corresponds to the duration of the laser pulse 504 when the intensity is greater than the specified flashing threshold value. Thus, the pulsewidth or duty of the flashing detection indication pulses 508 can be shorter than the corresponding on-time of the corresponding laser-source pulse 504.

Figure 6:
FIG. 6 illustrates an example of computer modeling of flashing on a display screen.

FIG. 6 shows an example of sixteen image frames being displayed on a display screen, such as when flashing is present and causing a displayed distortion artifact of saturated rows 602 of pixels, which are shown in FIG. 6 as corresponding bright horizontal lines. Such a distortion artifact of saturated rows 602 of pixels can itself be used as an indication of when and how much flashing is present, in an example. For example, the bottom right frame in FIG. 6 shows four saturated rows 602 of pixels (relatively more flashing), while the top right frame in FIG. 6 shows two saturated rows 602 of pixels (relatively less flashing). Such a distortion artifact indication of flashing can be detected by observing the image intensity of the displayed pixel on the display screen 108, or additionally or alternatively, by earlier upstream signal-processing of imaging signals being provided by the camera 106 to the video display driver 114 for generating an image for display on the display screen 108.

For example, if early upstream signal-processing of the imaging signals being provided by the camera 106 to the video display driver 114 indicate a partial or full row of camera imaging array pixels exceeding a saturation value indicative of flashing then a flashing indication can be generated upstream. In an example, the generated upstream flashing indication can be used to compensate for the flashing such that no higher intensity horizontal lines of saturated pixels need actually appear on the display screen 108. For example, for an appropriately high frame rate, a saturated partial or full row of pixels due to flashing can be substituted for by a non-saturated partial or full row of pixels appearing in an immediately preceding or similar slightly earlier frame, without significantly altering the visual perception presented to the user on the display screen 108. One or more other factors may be used in addition to a pixel-saturation exceeding a flashing threshold indicating flashing. In an example in which laser pulse issuance trigger information is available, then such information can be used, for example, to adjust the pixel-saturation flashing threshold. For example, lowering the pixel-saturation threshold indicating flashing during a time window corresponding to laser pulse issuances can help improve detecting flashing, whether by detecting a flashing-induced imaging distortion artifact, accumulating spectral information indicating flashing, or when using any combination of these or one or more other flashing indicators.

In FIG. 6, bright horizontal rows correspond to the displayed distortion artifact of saturated rows 602 of pixels. However, the signal processing circuitry 116 or display driver circuitry 114 may include a brightness compensation signal that automatically adjusts brightness of pixels of frames displayed on the display screen 108. In such a scenario, flashing may trigger such brightness compensation, resulting in a displayed distortion artifact of dark rows 602 of pixels. Such a dark partial or complete row distortion artifact may similarly be used to indicate whether and how much flashing is occurring. Additional compensation may include displaying the same partial or full row of pixels from an immediately preceding or slightly earlier frame, similar to the approach described earlier in response to the bright partial or full saturated row of pixels due to flashing. Additionally or alternatively, a separate indication of flashing (e.g., using the bandpass filtering and spectral accumulation, such as described above) can be used to adjust the brightness compensation to avoid or reduce the presence of the displayed distortion artifact of dark rows 602 of otherwise overcompensated pixels from flashing.

Figure 7:
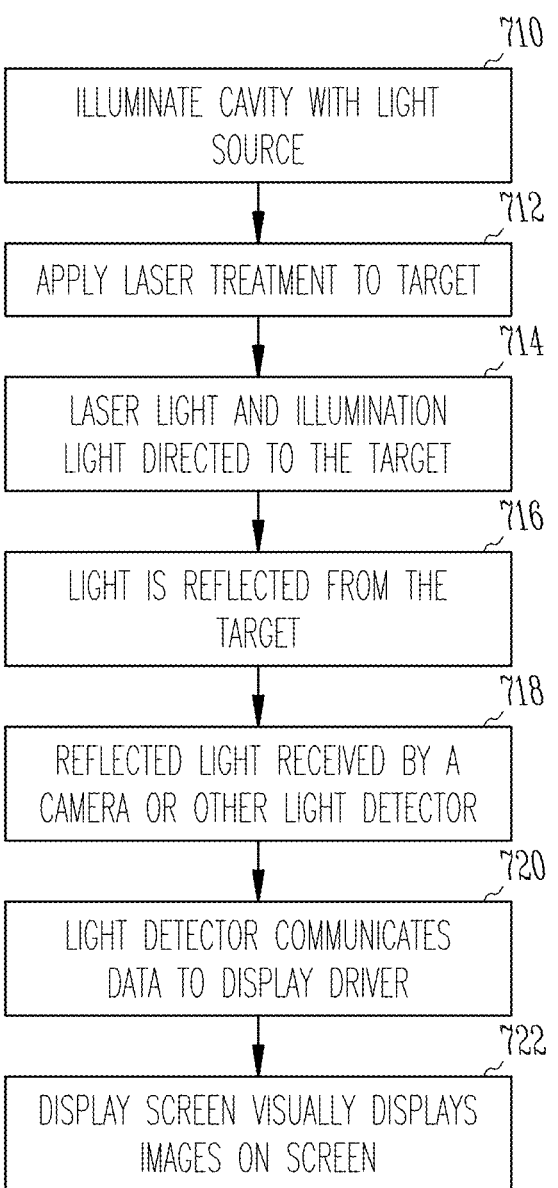
FIG. 7 depicts a method of imaging procedures.

FIG. 7 depicts an example of a method of providing laser treatment while concurrently imaging or spectroscopically analyzing a target region of interest, or both, such as in an endoscopic or similar minimally-invasive procedure.

At 710, a cavity or other target region of interest within a patient can be illuminated, such as can include using a broadband illumination light source 104 via an endoscope 110 such as to help with imaging or other visualization of the target region of interest.

At 712, laser energy from a laser source 112 can be applied to the target region of interest, such as concurrent with imaging of the target region of interest to allow the doctor or other user to observe the effect of the laser treatment via the imaging, such as via a display screen 108.

At 714, the laser energy and illumination light can be concurrently delivered to the target region of interest, such as via the endoscope 110.

At 716, as illumination light from the light source 104 and laser light from the laser source 112 are emitted, illumination light and laser light are reflected or otherwise scattered from the target 102.

At 718, the reflected light is received by the camera or light detector 106, such as for being transduced for imaging, for spectroscopic analysis of the target, or both. For example, spectroscopic analysis of the target can indicate whether the target being treated by the laser is a calculus ("stone") or tissue. Such information can be useful, for example, it can help the doctor or other user aim the laser toward the desired target, away from a nearby organ at risk, or both.

At 720, imaging information from the camera or light detector 106 can be signal-processed and provided to the display driver 114, such as for providing imaging display frame information for display on the display screen 108.

At 722, the display screen 108 can display an image or pictorial representation of data received via the light detector 114 and signal processed by the signal processing circuitry 116. FIG. 8a depicts an example of a method of detecting flashing.

At 810, illumination light and laser light can be endoscopically delivered into the cavity of an anatomical structure and can be directed endoscopically towards the target 102.

At 812, the camera or other light detector 106 can transduce detected response signal from the target into an electrical signal for signal-processing.

At 816, a flashing analyzer 120 can perform signal processing such as to help determine whether (or how much) flashing is present. This can include accumulating response light at wavelengths associated with flashing but not illumination, such as described herein. Additionally or alternatively, this can include detecting a distortion artifact associated with flashing, such as bright partial or full rows of saturated pixels, or dark partial or full rows of pixels overcompensated for brightness due to flashing.

At 824, based on an indication from the flashing analyzer 120 of whether (or how much) flashing is present, the flashing analyzer 120 can generate a flashing alert, such as which can be provided to a user via a visual, audible, haptic, or other alert indicator.

At 826, based on an indication from the flashing analyzer 120 of whether (or how much) flashing is present, the flashing analyzer 120 can generate a flashing control signal.

At 828, the flashing control signal can be used to control one or more components that can be included in or coupled to the system 100. For example, the flashing control signal can be used to control one or more of the illumination light source, the laser source, the display driver, the display screen, a display compensation signal (e.g., brightness compensation), or a spectroscopic target analyzer. For example, the illumination light source 104 or the laser source 112, can be controlled by flashing control signal (e.g., controller circuitry 116), such as to increase or decrease the amount of illumination light or laser light emitted to reduce the occurrence or amount of flashing. Additionally or alternatively, the display driver or display screen can be controlled, such as to substitute from an immediately preceding or slightly earlier frame, corresponding pixels into a frame subject to flashing. Additionally or alternatively, a display compensation signal such as (a brightness compensation signal) can be adjusted during flashing to avoid over-compensating for brightness due to flashing leading to dark horizontal rows being displayed on the display screen. Additionally or alternatively, a spectroscopic target analyzer can be controlled, such as to avoid spectroscopically sampling the target region during flashing occurrences. Such spectroscopic analysis can be helpful in distinguishing whether the tissue or a biological calculus is being targeted, which can be helpful to the user in properly aiming the laser toward the target region (e.g., calculus) to be laser-treated or away from a non-target region (e.g., tissue) for which treatment is to be avoided, as appropriate to a particular procedure.

FIG. 8b depicts another example of a method of detecting and responding to laser-sourced flashing.

At 830, a flashing component detector 118 can receive a response light signal from the target region of interest, such as via transducing by the camera or other light detector 106 into an electrical imaging or other representation of the response light signal.

At 832, a laser-source flashing component of the transduced response light signal can be separated from the non-flashing component of the response light signal, such as using a bandpass or other wavelength-specific filter, such as described herein, and integrating or otherwise accumulating the response over the wavelengths of interest representing a flashing component of the response light signal.

At 834, the resulting accumulated response signal can be compared to one or more criteria, such as a specified threshold value.

At 836, a spectroscopic analyzer can suppress spectroscopic signal sampling of the target region during occurrences of flashing, which could otherwise interfere with proper spectroscopic analysis, such as to determine whether the target constitutes a biological calculus to be laser-treated or tissue for which laser-treatment is to be avoided.

FIG. 8c illustrates an example of portions of a method in which a spectrometer can be used (e.g., without requiring a separate wavelength filter) to separate wavelengths of light, such as to determine whether (or how much) flashing is present.

At 840, the spectrometer can measure the wavelengths received from the target response signal.

At 842, the spectrometer 402 can then separate the wavelengths associated with the laser-source flashing from those wavelengths associated with a non-flashing component of the target response signal (e.g, with a response light wavelength filter 302), such as to permit accumulation of energy or intensity at wavelengths associated with the flashing component for comparison to a threshold value at 844.

At 846, the non-flashing components can be qualified (e.g., disregarded, not sampled, or suppressed) when the comparison at 844 indicates that flashing component exceeds the flashing threshold value, thereby indicating that flashing is present and may be affecting the non-flashing components that were spectroscopically measured.

FIG. 8d illustrates an example of portions of a method in which a distortion artifact or other component of an image of the target, captured and being signal processed for image display of the target on a display screen, indicates that flashing is occurring.

At 850, response light from the target region of interest can be transduced into a response signal by the camera or other light detector 106.

At 852, a distortion or other artifact indicating flashing can be detected. For example, a distortion artifact can include a partial or full horizontal row of bright (e.g., saturated) pixels, either on the display screen, or at an imaging array of the camera or other light detector 106, or at an intermediate signal processing component therebetween. An additional or alternative example of a distortion artifact can include a partial or full horizontal row of dark (e.g., over-brightness-compensated) pixels, either on the display screen, or at an imaging array of the camera or other light detector 106, or at an intermediate signal processing component therebetween, in an example in which brightness auto-compensation is included, but which can potentially result in over-compensation when flashing occurs. An additional or alternative example of an artifact can include using the brightness compensation itself to detect and indicate the presence of flashing.

At 854, in response to detecting flashing, the display image can be compensated. For example, this can involve substituting one or more partial or complete rows of saturated (or overcompensated pixels) with corresponding pixels from an immediately preceding frame or a similarly recent frame. This can still provide relatively consistent accuracy for visualization, while suppressing the effect of flashing or of overcompensation (e.g., of auto-brightness compensation) due to flashing. At 856, in response to detecting flashing, one or more other components included in or coupled to the system can be compensated or otherwise controlled, such as the light source, the laser source, the display driver, the display screen, or the spectroscopic analyzer, such as described elsewhere herein.

Figure 9:
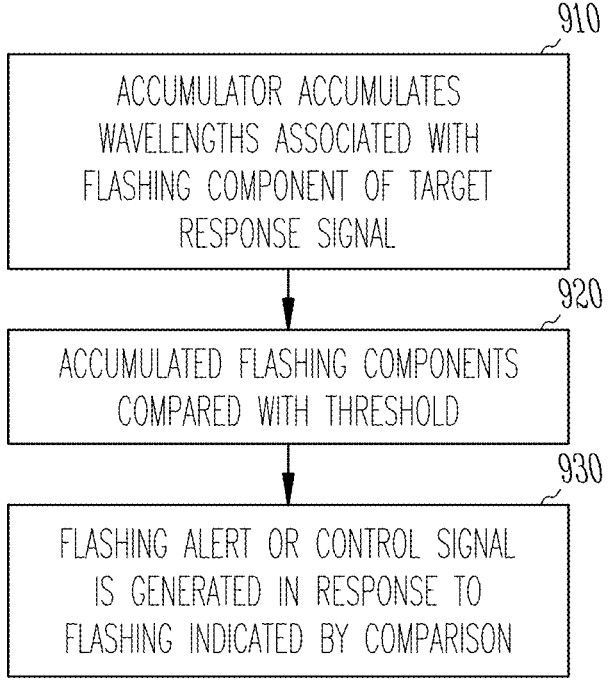
FIG. 9 illustrates a method using an accumulator for detecting flashing.

FIG. 9 illustrates an example of portions of a method in which a flashing analyzer can be used for detecting flashing.

At 910, an accumulator can accumulate wavelengths of the target response signal that are associated with a flashing component of the target response signal and are not associated with a non-flashing component of the target response signal.

At 920, the accumulated wavelengths associated with a flashing component can be compared to one or more criteria, such as a threshold value, such as to determine whether flashing is occurring.

At 930, a flashing alert or control signal can be generated in response to the comparison indicating that flashing is occurring. Optionally, the accumulator 304 stores, either transitorily or for communication to a longer term log, data related to the laser sourced flashing. Such logged data can include, for example, accumulated spectral energies in the wavelengths associated with flashing, durations of the same, or both. Such logged flashing information can be used to augment non-flashing spectrometer information about the response light from the target, such as which is used to spectroscopically analyze the material type (e.g., calculus or tissue) of the target. Because certain types of calculi cause more flashing than other types of calculi, information about whether flashing is occurring can be used to help differentiate between different calculi types, such as by augmenting non-flashing spectrometric data being analyzed.

What is claimed is:

1. A system for endoscopically imaging a first target of a patient, using a light source and a light detector, and for laser-treating a same or different second target of the patient, using a laser source, the system comprising:

signal processing circuitry, couplable to the light detector to receive a target response signal indicative of light received from the patient in response to illumination by at least one of the light source and the laser source, the signal processing circuitry including:

a target response signal laser-source flashing component detector, to detect a laser-source flashing component of the target response signal;

a flashing analyzer, to receive the laser-source flashing component of the target response signal from the target response signal laser-source flashing component detector, and to generate a flashing alert or a flashing control signal based at least in part on an indication of an amount of the laser-source flashing component of the target response signal; and a controller circuitry, coupled to the flashing analyzer, configured to control a laser source flashing-induced distortion artifact, the controller circuitry including:

a laser source control output configured to provide a laser source control signal to control a laser-source pulse amount based at least in part on the flashing control signal, to control the laser-source flashing-induced distortion artifact on a display screen.

2. The system of claim 1, wherein the laser-source flashing component detector includes at least one of:

a filter, to separate the laser-source flashing component of the target response signal from a non-flashing component of the target response signal;

a spectrometer, to spectrometrically separate wavelengths associated with the laser-source flashing component of the target response signal from wavelengths associated with the non-flashing component of the target response signal; or upstream signal-processing of the display screen, to generate the laser-source flashing component of the target response signal based on the laser-source flashing-induced distortion artifact of an imaging display signal.

3. The system of claim 1, wherein the flashing analyzer includes an accumulator to cumulate portions associated with the laser-source flashing component of the target response signal to generate the indication of the amount of the laser-source flashing component.

4. The system of claim 3, wherein the accumulator cumulates the portions including at least one of:

intensities associated with corresponding wavelengths associated with the laser-source flashing component of the target response signal;

durations associated with corresponding wavelengths associated with the laser-source flashing component of the target response signal;

intensities associated with corresponding pixels associated with the laser-source flashing component of the target response signal; or durations associated with corresponding pixels associated with the laser-source flashing component of the target response signal.

5. The system of claim 1, wherein the light detector includes an imager, and further comprising:

an imaging display interface, to couple the imager to the display screen to display an image produced by the imager on the display screen; and the controller circuitry, to receive the flashing control signal, to control at least one of the laser source, the light source, the light detector, the imager, or the display screen to manage the laser-source flashing-induced distortion artifact on the display screen based at least in part on the flashing control signal.

6. The system of claim 5, wherein the controller circuitry includes a light source control output to provide a light source control signal to control a light source output intensity of the light source, based at least in part on the flashing control signal, to manage the laser-source flashing-induced distortion artifact on the display screen.

7. The system of claim 5, wherein the controller circuitry includes an imager control output to control an accumulation time of the imager, based at least in part on the flashing control signal, to manage the laser-source flashing-induced distortion artifact on the display screen.

8. The system of claim 5, wherein the controller circuitry includes a display control output to control display of one or more pixels or frames of an image produced by the imager based at least in part on the flashing control signal to manage the laser-source flashing-induced distortion artifact on the display screen.

9. The system of claim 8, wherein the display control output is configured to at least one of attenuate or suppress one or more saturated rows of pixels of the image produced by the imager based at least in part on the flashing control signal to manage the laser-source flashing-induced distortion artifact on the display screen.

10. The system of claim 8, wherein the display control output is configured to at least one of attenuate or suppress one or more frames of the image produced by the imager based at least in part on the flashing control signal to manage the laser-source flashing-induced distortion artifact on the display screen.

11. The system of claim 1, wherein the laser-source pulse amount, controlled based at least in part on the flashing control signal, includes at least one of pulse energy, pulse width, pulse shape, or pulse frequency, being controlled based at least in part on the flashing control signal.

12. The system of claim 1, wherein the laser source control output provides the laser source control signal to control the laser source to reduce an energy of the laser source by adjusting the laser-source pulse amount based at least in part on the flashing control signal and to manage the laser-source flashing-induced distortion artifact on the display screen.

13. The system of claim 1, wherein the signal processing circuitry includes a calculus or other anatomical detection or characterization analyzer to generate an indication of a detection or characterization of a particular type of target based at least in part on the flashing control signal.

14. The system of claim 13 wherein the light detector includes an imager, and including:

an imaging display interface, to couple the imager to the display screen to display at least the target; and the controller circuitry, coupled to the flashing analyzer to receive the flashing control signal, to control at least one of the laser source, the light source, the light detector, the imager, or the display screen to manage a visualization of the target by managing the laser-source flashing-induced distortion artifact on the display screen based at least in part on the flashing control signal.

15. A system for endoscopically imaging a first target of a patient, using a light source and a light detector, and for laser-treating a same or different second target of the patient, using a laser source, the system comprising:

signal processing circuitry, couplable to the light detector to receive a target response signal indicative of light received from the patient in response to illumination by at least one of the light source and the laser source, the signal processing circuitry including:

a target response signal laser-source flashing component detector configured to detect a laser-source flashing component of the target response signal;

a flashing analyzer configured perform signal processing to detect the laser-source flashing component of the target response signal from the target response signal flashing component detector, and to generate a flashing alert or flashing control signal based at least in part on an indication of an amount of the laser-source flashing component of the target response signal; and a calculus or other anatomical analyzer to generate an indication of a detection or characterization of a particular type of target based at least in part on the flashing control signal.

16. The system of claim 15, wherein the calculus or other anatomical analyzer includes a target analyzer.

17. The system of claim 15, wherein the light detector includes an imager, the system including:

an imaging display interface coupling the imager to a display screen to display at least the target.

18. The system of claim 15, wherein the light detector includes an imager, the system including:

controller circuitry, coupled to the flashing analyzer to receive the flashing control signal, to control at least one of the laser source, the light source, the light detector, the imager, or a display screen to manage a visualization of the target by managing a laser-source-flashing induced distortion artifact on the display screen.

19. The system of claim 15, wherein the controller circuitry is configured to manage a visualization of the target based at least in part on the flashing control signal.

* * * * *